United States Patent
Park et al.

(10) Patent No.: US 11,298,009 B2
(45) Date of Patent: Apr. 12, 2022

(54) ELECTRODE SELECTION DEVICE FOR SELECTING OPTIMAL ELECTRODES TO COMMUNICATE WITH CAPSULE ENDOSCOPE, AND OPERATION METHOD THEREOF

(71) Applicant: Electronics and Telecommunications Research Institute, Daejeon (KR)

(72) Inventors: Mi Jeong Park, Sejong-si (KR); Hyung-Il Park, Daejeon (KR); Tae Wook Kang, Daejeon (KR); Sung Eun Kim, Daejeon (KR); Hyuk Kim, Daejeon (KR); Kwang Il Oh, Daejeon (KR); Jae-Jin Lee, Daejeon (KR); In Gi Lim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 285 days.

(21) Appl. No.: 16/402,164

(22) Filed: May 2, 2019

(65) Prior Publication Data
US 2019/0335984 A1 Nov. 7, 2019

(30) Foreign Application Priority Data

May 3, 2018 (KR) .................. 10-2018-0051490
Aug. 30, 2018 (KR) .................. 10-2018-0103017

(51) Int. Cl.
*A61B 1/00* (2006.01)
*A61B 1/04* (2006.01)
*H04B 13/00* (2006.01)

(52) U.S. Cl.
CPC .......... *A61B 1/041* (2013.01); *A61B 1/00011* (2013.01); *H04B 13/005* (2013.01)

(58) Field of Classification Search
CPC ... A61B 1/041; A61B 1/00011; A61B 1/0001; A61B 1/0009; A61B 2562/162;
(Continued)

(56) References Cited

U.S. PATENT DOCUMENTS 8,467,431 B2 6/2013 Park et al.
8,798,049 B2 8/2014 Lim et al.
(Continued)

FOREIGN PATENT DOCUMENTS

| KR | 10-1063859 B1 | 9/2011 |
| KR | 10-1580479 B1 | 12/2015 |
| KR | 10-1731597 B1 | 4/2017 |

*Primary Examiner* — Timothy J Neal
*Assistant Examiner* — Sung Ham
(74) *Attorney, Agent, or Firm* — Rabin & Berdo, P.C.

(57) ABSTRACT

Provided is and electrode selection device communicating with a capsule endoscope. The device includes an analog front end configured to recover first data based on first signals transmitted from the capsule endoscope to a first electrode and a second electrode, recover second data based on second signals transmitted from the capsule endoscope to the first electrode and a third electrode, and recover third data based on third signals transmitted from the capsule endoscope to the second electrode and the third electrode, and a digital receiver configured to calculate a first correlation value between the first and second electrodes, a second correlation value between the first and third electrodes, and a third correlation value between the second and third electrodes based on the first to third data. The digital receiver calculates first to third correlation sums, and selects a receiving electrode pair based on the first to third correlation sums.

9 Claims, 10 Drawing Sheets

(58) Field of Classification Search
CPC .......... A61B 1/00147; A61B 1/00158; A61B 5/0028; A61B 5/036; A61B 5/06; A61B 5/063; A61B 5/073; A61B 5/6861; H04B 13/005; H04N 2005/2255
USPC .............................. 128/897, 899, 920; 600/7
See application file for complete search history.

(56) References Cited

U.S. PATENT DOCUMENTS

| | | | | |
|---|---|---|---|---|
| 2007/0255087 | A1* | 11/2007 | Minai | A61B 1/041 600/12 |
| 2008/0318541 | A1* | 12/2008 | Kimoto | A61B 5/0031 455/277.1 |
| 2009/0137883 | A1* | 5/2009 | Chiba | A61B 1/041 600/302 |
| 2012/0128036 | A1* | 5/2012 | Kang | H04B 13/005 375/144 |
| 2012/0201235 | A1* | 8/2012 | Lim | A61B 1/00016 370/349 |
| 2015/0196769 | A1* | 7/2015 | Stahmann | A61N 1/37288 607/32 |
| 2018/0026729 | A1 | 1/2018 | Lim et al. | |

* cited by examiner

FIG. 8

| | E1 | E2 | E3 | E4 | E5 | E6 | E7 | E8 | Correlation Sum |
|---|---|---|---|---|---|---|---|---|---|
| E1 | -- | 0 | 285 | 71 | 369 | 383 | 381 | 165 | 1654 |
| E2 | 0 | -- | 371 | 191 | 365 | 384 | 377 | 90 | 1778 |
| E3 | 285 | 371 | -- | 377 | 0 | 384 | 382 | 78 | 1877 |
| E4 | 71 | 191 | 377 | -- | 384 | 384 | 381 | 0 | 1788 |
| E5 | 369 | 365 | 0 | 384 | -- | 380 | 250 | 382 | 2130 |
| E6 | 383 | 384 | 384 | 384 | 380 | -- | 337 | 384 | 2636 |
| E7 | 381 | 377 | 382 | 381 | 250 | 337 | -- | 384 | 2492 |
| E8 | 165 | 90 | 78 | 0 | 382 | 384 | 384 | -- | 1483 |

ELECTRODE SELECTION DEVICE FOR SELECTING OPTIMAL ELECTRODES TO COMMUNICATE WITH CAPSULE ENDOSCOPE, AND OPERATION METHOD THEREOF

CROSS-REFERENCE TO RELATED APPLICATIONS

This U.S. non-provisional patent application claims priority under 35 U.S.C. § 119 of Korean Patent Application Nos. 10-2018-0051490, filed on May 3, 2018, and 10-2018-0103017, filed on Aug. 30, 2018, the entire contents of which are hereby incorporated by reference.

BACKGROUND

The present disclosure herein relates to an electrode selection device and an operation method thereof, and more particularly, to an electrode selection device for selecting optimal electrodes to communicate with a capsule endoscope, and an operation method thereof.

In order to transmit the image data generated by the imaging of the capsule endoscope to a receiver, human body communication technology is used instead of Radio Frequency (RF) communication technology. A capsule endoscope using human body communication technology transmits data to a receiver outside the human body using the human body as a medium. Generally, the receiver receives data through electrodes attached to the human body surface.

Capsule endoscope moves continuously along the digestive tract by the peristalsis of the organs. Due to the movement of the capsule endoscope, the pair of optimal electrodes that may receive data stably and accurately from the capsule endoscope is changed in real time. Therefore, there is a demand for a technique capable of selecting a pair of optimal electrodes.

SUMMARY

The present disclosure is to provide an electrode selection device for selecting optimal electrodes to communicate with a capsule endoscope, and an operation method of thereof.

An embodiment of the inventive concept provides an electrode selection device communicating with a capsule endoscope, the device including: an analog front end configured to recover first data based on first signals transmitted from the capsule endoscope to a first electrode and a second electrode, recover second data based on second signals transmitted from the capsule endoscope to the first electrode and a third electrode, and recover third data based on third signals transmitted from the capsule endoscope to the second electrode and the third electrode; and a digital receiver configured to calculate, based on the first to third data, a first correlation value between the first and second electrodes, a second correlation value between the first and third electrodes, and a third correlation value between the second and third electrodes, wherein the digital receiver calculates a first correlation sum obtained by adding first and second correlation values generated using the first electrode, a second correlation sum obtained by adding the first and third correlation values generated using the second electrode, and a third correlation sum obtained by adding the second and third correlation values generated using the third electrode, and selects a receiving electrode pair among the first to third electrodes based on the first to third correlation sums.

In an embodiment of the inventive concept, an operation method of an electrode selection device communicating with a capsule endoscope includes: recovering first data based on first signals transmitted from the capsule endoscope to a first electrode and a second electrode and calculating a first correlation value between the first electrode and the second electrode based on the first data; recovering second data based on second signals transmitted from the capsule endoscope to the first electrode and a third electrode and calculating a second correlation value between the first electrode and the third electrode based on the second data; recovering third data based on third signals transmitted from the capsule endoscope to the second electrode and the third electrode and calculating a third correlation value between the first electrode and the third electrode based on the third data; calculating a first correlation sum of the first electrode, a second correlation sum of the second electrode, and a third correlation sum of the third electrode by separately adding the first to third correlation values; and selecting a receiving electrode pair among the first to third electrodes based on the first to third correlation sums.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings:

FIG. 8 is a table exemplarily showing correlation values between electrodes and correlation sums of electrodes according to the operations of FIG. 6;

DETAILED DESCRIPTION

In the following, embodiments of the inventive concept will be described in detail so that those skilled in the art easily carry out the inventive concept.

Figure 1:
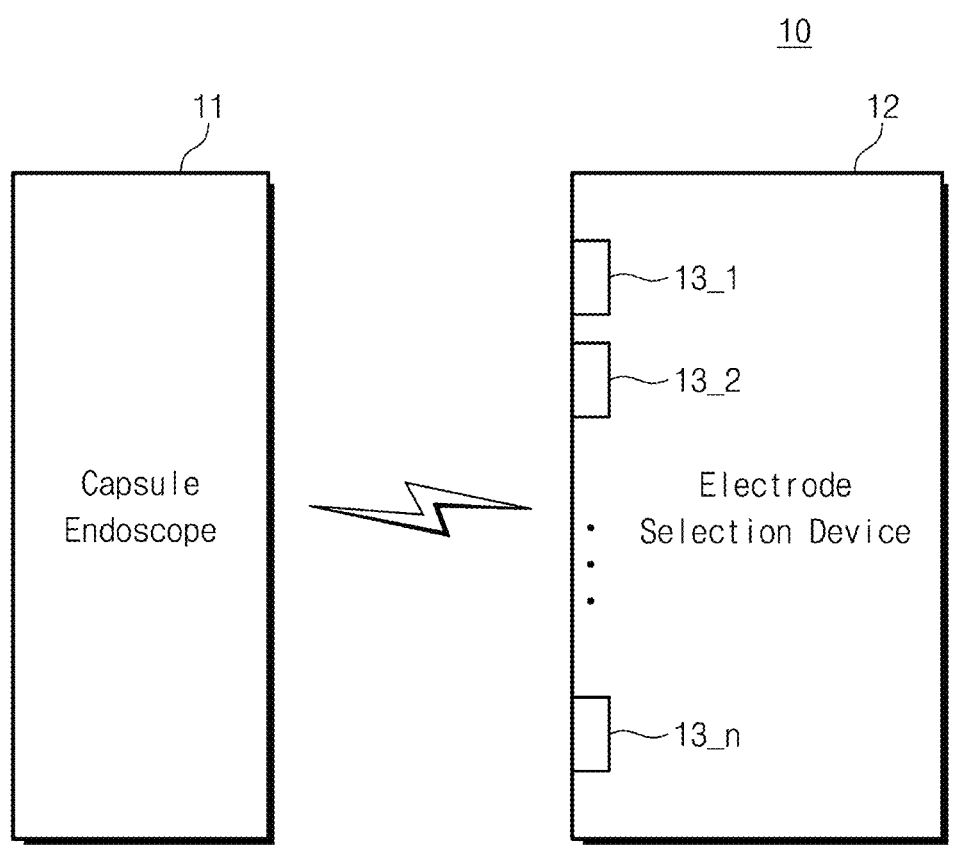
FIG. 1 is a block diagram illustrating an exemplary capsule endoscope system according to an embodiment of the inventive concept.

FIG. 1 is a block diagram illustrating an exemplary capsule endoscope system according to an embodiment of the inventive concept. A capsule endoscope system 10 may include a capsule endoscope 11 and an electrode selection device 12.

The capsule endoscope 11 may perform imaging inside a living body of a human being (or an animal, the living body is assumed as the human body inhere) while moving along the digestive organs of the living body by the peristaltic movement of the organs. Further, the capsule endoscope 11 may generate image data by imaging, and may transmit the generated image data to the electrode selection device 12 outside the human body. Although not shown in FIG. 1, the capsule endoscope 11 may include an image sensor, a light source, a transmitter, transmission electrodes, and a battery.

Communication between the capsule endoscope 11 and the electrode selection device 12 may be performed through a method of transmitting signals to the electrode selection device 12 using the human body as a medium. A potential difference may be generated at the transmission electrodes by the data transmission of the capsule endoscope 11. The capsule endoscope 11 uses a method of transmitting a signal by causing a change in an electric field according to a potential difference. The electrode selection device 12 may receive data by detecting the current.

The electrode selection device 12 may include first to n-th electrodes 13_1 to 13_n for receiving signals from the capsule endoscope 11. The first to n-th electrodes 13_1 to 13_n may be referred to as first to n-th receiving electrodes. Here, the number of the first to the n-th electrodes 13_1 to 13_n may be at least three, and n is a natural number of at least three.

Since the capsule endoscope 11 moves along the digestive organs of the human body, the optimal channel among channels between the transmission electrodes of the capsule endoscope 11 and the first to nth electrodes 13_1 to 13_n of the electrode selection device 12 may be changed according to the movement of the capsule endoscope 11. Depending on the position of the capsule endoscope 11 with respect to the first to n-th electrodes 13_1 to 13_n, an error may occur in the communication between the capsule endoscope 11 and the electrode selection device 12. For example, if the capsule endoscope 11 and the first to n-th electrodes 13_1 to 13_n are too close to each other, the intensity of the signals inputted to the first to the n-th electrodes 13_1 to 13_n is large, so that distortion of the signal may occur (that is, saturation phenomenon). For another example, if the directions of the transmission electrodes of the capsule endoscope 11 and the directions of the first to n-th electrodes 13_1 to 13_n are perpendicular to each other, communication between the capsule endoscope 11 and the electrode selection device 12 may not be performed.

Therefore, in order to receive image data stably and accurately from the capsule endoscope 11, the electrode selection device 12 according to the embodiment of the inventive concept may select the pair of optimal electrodes among the first to n-th electrodes 13_1 to 13_n. The pair of optimal electrodes may be referred to as a pair of receiving electrodes. For this, before transmitting the image data, the capsule endoscope 11 may generate a signal based on the reference data and transmit the signal to the electrode selection device 12. The electrode selection device 12 may select the pair of optimal electrodes among the first to n-th electrodes 13_1 to 13_n based on the received reference data. Here, the reference data may include a predetermined pattern, which is determined in advance, for selecting a pair of optimal electrodes. The reference data may be stored in the capsule endoscope 11 and the electrode selection device 12, respectively.

Figure 2:
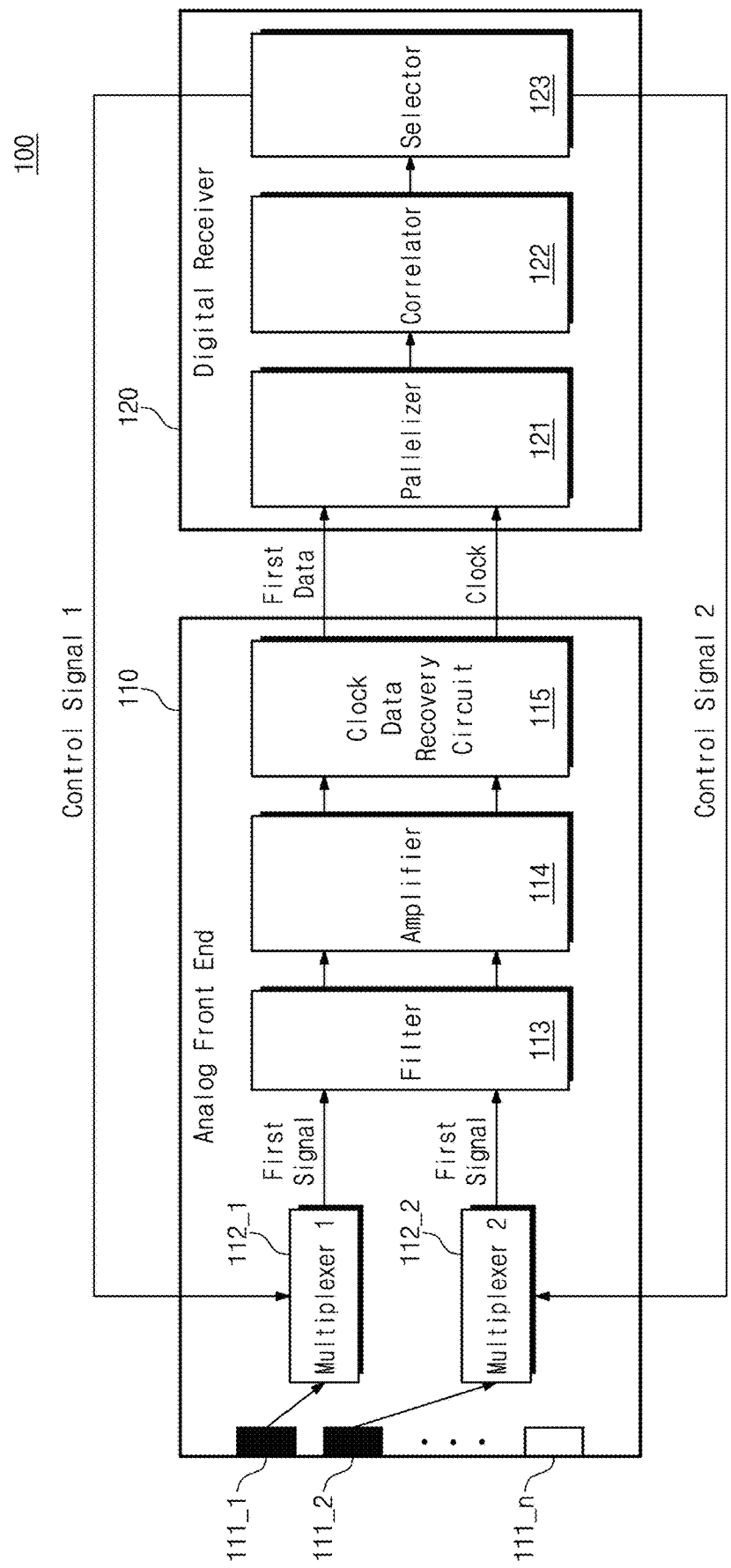
FIG. 2 is a block diagram exemplarily illustrating an electrode selection device of FIG. 1.

FIG. 2 is a block diagram exemplarily illustrating an electrode selection device of FIG. 1. FIG. 2 will be described with reference to FIG. 1. The electrode selection device 100 of FIG. 2 may be substantially the same as the electrode selection device 12 of FIG. 1. The electrode selection device 100 may include an analog front end 110 and a digital receiver 120.

The analog front end 110 may include first to n-th electrodes 111_1 to 111_n for receiving signals from the capsule endoscope 11, first and second multiplexers 112_1 and 112_2, a filter 113, an amplifier 114, and a clock data recovery circuit 115. Here, the first to the n-th electrodes 111_1 to 111_n may be substantially the same as the first to the n-th electrodes 13_1 to 13_n.

The analog front end 110 may convert signals received in analog form into digital form signals and may transmit the digital form signals to the digital receiver 120. The analog front end 110 may recover data based on the signals transmitted from the capsule endoscope 11.

The first multiplexer 112_1 may select one of the first to the n-th electrodes 111_1 to 111_n according to the first control signal. The second multiplexer 112_2 may select another one of the first to the n-th electrodes 111_1 to 111_n according to the second control signal. The first and second control signals may be generated by the digital receiver 120 and will be described below. One electrode selected by the first multiplexer 112_1 and another electrode selected by the second multiplexer 112_2 may be different from each other. Until the pair of optimal electrodes is determined by the digital receiver 120, the first and second multiplexers 112_1 and 112_2 may repeatedly select any two of the first to n-th electrodes irrespective of order. In FIG. 2, by way of example, it is assumed that the first multiplexer 112_1 selects the first electrode 111_1 and the second multiplexer 112_2 selects the second electrode 111_2.

The first and second multiplexers 112_1 and 112_2 may provide the first signals to the filter 113 through the first and second electrodes 111_1 and 111_2. For example, the first signals may be transmitted from the capsule endoscope 11 to the first and second electrodes 111_1 and 111_2 in a differential manner.

The filter 113 may block or pass only signals in a certain frequency range. The filter 113 may remove noise that may be added to the first signals in the process of being transmitted from the capsule endoscope 11 to the first and second electrodes 111_1 and 111_2 through the human body.

The amplifier 114 may amplify the magnitudes of the filtered first signals. The clock data recovery circuit 115 may recover or reconfigure the clock and first data based on the amplified first signals and may output or provide the clock and first data to the digital receiver 120. For example, the clock may be used to sample the first data.

Referring to FIG. 2, the digital receiver 120 may include a parallelizer 121 (i.e., S2P block), a correlator 122, and a selector 123. The digital receiver 120 may receive clock and data from the analog front end 110 and may determine the characteristics of the channels according to the first to nth electrodes 111_1 through 111_n. The digital receiver 120 may control the first and second multiplexers 112_1 and 112_2 to select the optimal channel based on the characteristics of the channels.

The parallelizer 121 may convert the serial-type data transmitted by one bit into parallel-type data composed of a plurality of bits. The parallelizer 121 may parallelize or sample the first data based on the clock. For example, the parallelizer 121 may include flip-flops, latches, and the like to store the parallelized bits. The parallelizer 121 may provide parallel-type converted data to the correlator 122. Depending on the situation, the digital receiver 120 may not include the parallelizer 121. For example, the digital receiver 120 may process serial-type data transmitted by one bit without conversion into parallel data. The serial-type data transmitted by one bit from the digital receiver 120 may be provided to the correlator 122 as it is.

In order to grasp the characteristics of the first and second electrodes 111_1 and 111_2 selected by the first and second multiplexers 112_1 and 112_2, the correlator 122 may calculate a correlation value between the first and second electrodes 111_1 and 111_2. For example, the correlator 122 may calculate a first correlation value between the first and second electrodes 111_1 and 111_2 using the first signals transmitted through the first and second electrodes 111_1 and 111_2. Here, the first correlation value may be calculated by comparing the first data with the reference data reconstructed based on the first signals. For example, the first correlation value may be proportional to the degree of similarity between the first data and the reference data. Accordingly, as the first correlation value is higher, the electrode selection device 100 may more reliably and accurately receive data from the capsule endoscope 11 through the first and second electrodes 111_1 and 111_2.

The selector 123 may control the first and second multiplexers 112_1 and 112_2. The selector 123 may generate a first control signal provided to the first multiplexer 112_1. The selector 123 may generate a second control signal provided to the second multiplexer 112_2. In FIG. 2, it is shown that the first and second electrodes 111_1 and 111_2 of the first and second multiplexers 112_1 and 112_2 are selected according to the first and second control signals. However, the selector 123 may generate the first and second control signals so that the first and second multiplexers 112_1 and 112_2 select different electrodes.

Figure 3:
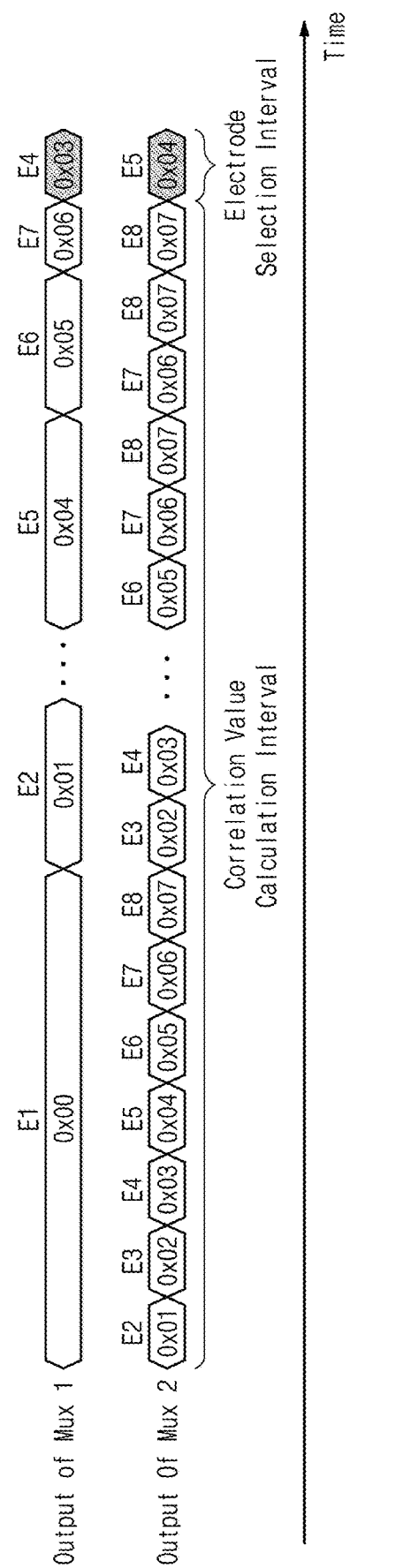
FIG. 3 exemplarily illustrates output signals of first and second multiplexers controlled by the selector of FIG. 2.

FIG. 3 exemplarily illustrates output signals of first and second multiplexers controlled by the selector of FIG. 2. FIG. 3 will be described with reference to FIG. 2. In FIG. 3, it is assumed that the number of the first to n-th electrodes 111_1 to 111_n in FIG. 2 is eight.

E1 to E8 may represent the first to eighth electrodes 111_1 to 111_8, respectively. 0x00 to 0x07 may be the address information of the first to eighth electrodes 111_1 to 111_8. The output signals of the first and second multiplexers 112_1 and 112_2 will be described along the time axis.

For example, the first and second multiplexers 112_1 and 112_2 may first select the first and second electrodes 111_1 and 111_2 according to the control of the selector 123. The analog front end 110 may recover the clock and data from the signals transmitted to the first and second electrodes 111_1 and 111_2 and the digital receiver 120 may receive the recovered clock and data. Then, the first and second multiplexers 112_1 and 112_2 may select the first and third electrodes 111_1 and 111_3 according to the control of the selector 123. The analog front end 110 may recover the clock and data from the signals transmitted to the first and third electrodes 111_1 and 111_3 and the digital receiver 120 may receive the recovered clock and data.

In a similar manner, the first and second multiplexers 112_1 and 112_2 may repeatedly select the other electrodes according to the control of the selector 123. The analog front end 110 may repeatedly recover clock and data from signals transmitted to other electrodes. The digital receiver 120 may repeatedly receive the recovered clock and data. In FIG. 3, since n is assumed to be 8, the first and second multiplexers 112_1 and 112_2 may select the different electrodes among the first to eighth electrodes 111_1 to 111_8 in total 28 times (8C2).

In an embodiment, while the first multiplexer 112_1 selects and holds the first electrode 111_1, the second multiplexer 112_2 may sequentially select the remaining electrodes 111_2 to 111_8. After the second multiplexer 112_2 selects all of the remaining electrodes 111_2 to 111_8, the first multiplexer 112_1 may select the second electrode 111_2. While the first multiplexer 112_1 selects and holds the second electrode 111_2, in order to prevent previously selected combinations of electrodes from being selected again, the second multiplexer 112_2 may sequentially select the remaining electrodes 111_3 to 111_8 except for the first and second electrodes 111_1 and 111_2.

If the electrode selection is repeated in a similar manner, the first and second multiplexers 112_1 and 112_2 may select different electrodes in order as shown in FIG. 3, and select a combination of the total of 28 electrodes (8C2). However, the order in which the selector 123 selects the first to eighth electrodes is an exemplary one and is not limited to that shown in FIG. 3.

In the correlation value calculation interval, the first and second multiplexers 112_1 and 112_2 may select different electrodes of the first to eighth electrodes 111_1 to 111_8 according to the control of the selector 123. Also, in the correlation value calculation interval, the digital receiver 120 may repeatedly calculate the correlation value between the electrodes selected by the first and second multiplexers 112_1 and 112_2.

The correlation value calculation interval shown in FIG. 3 is an exemplary one. Since the number of electrodes 111_1 to 111_8 is assumed to be 8 in FIG. 3, the time for which the first and second multiplexers 112_1 and 112_2 may repeat the 28 selections may correspond to the correlation value calculation interval. As the number of the first to n-th electrodes 111_1 to 111_n increases, the correlation value calculation interval may also expand.

In the electrode selection interval, the digital receiver 120 may select a pair of optimal electrodes based on the correlation values during the correlation value calculation interval of each frame. Illustratively, E4 and E5 are shown as selected in FIG. 3. Although not shown in FIG. 3, after E4 and E5 are selected, the digital receiver 120 may select a new pair of optimal electrodes based on the new correlation values during the new correlation value calculation interval.

Figure 4:
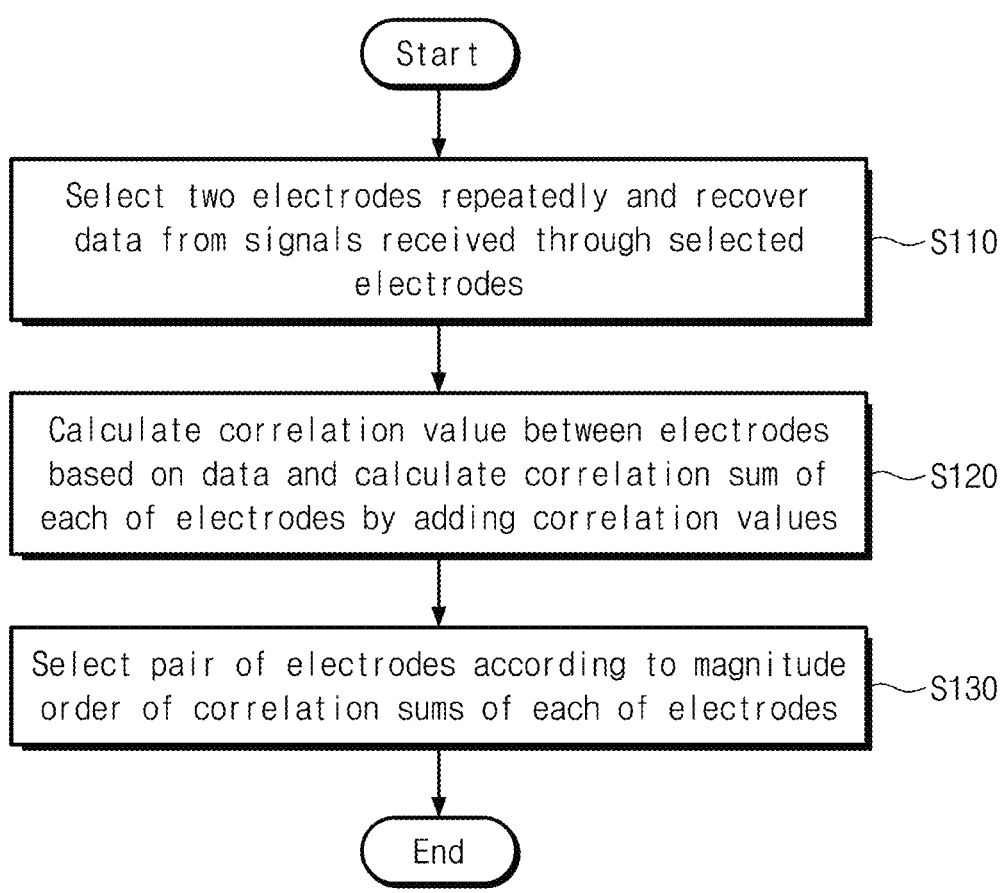
FIG. 4 is a flowchart exemplarily illustrating an operation method of the electrode selection device of FIG. 2.

FIG. 4 is a flowchart exemplarily illustrating an operation method of the electrode selection device of FIG. 2. FIG. 4 will be described with reference to FIGS. 2 to 3. In FIG. 4, it is assumed that the number of the first to n-th electrodes 111_1 to 111_n in FIG. 2 is eight.

In operation S110, the analog front end 110 repeatedly may select the two electrodes according to the control of the digital receiver 120, and then, recover data based on the signals transmitted from the capsule endoscope 11 to the two electrodes. For example, the first and second multiplexers 112_1 and 112_2 may select the first and second electrodes 111_1 and 111_2, and the analog front end 110 may recover the clock and first data from the first signals transmitted to the first and second electrodes 111_1 and 111_2. Then, the first and second multiplexers 112_1 and 112_2 may select the first and third electrodes 111_1 and 111_3, and the analog front end 110 may recover the clock and second data from the second signals transmitted to the first and third electrodes 111_1 and 111_3.

In a similar manner, the first and second multiplexers 112_1 and 112_2 may repeatedly select the other electrodes. The analog front end 110 may repeatedly recover clock and data from signals transmitted to other electrodes. Operation S110 will be described in more detail in FIG. 5

In operation S120, the digital receiver 120 may calculate the correlation value between the electrodes based on the clock and data recovered in operation S110, and calculate the correlation sum of each of the first to eighth electrodes 111_1 to 111_8 by individually adding the correlation values.

For example, the correlator 122 may compare the first data according to the selection of the first and second electrodes 111_1 and 111_2 with the reference data and calculate a first correlation value between the first and second electrodes 111_1 and 111_2. Then, the correlator 122 may compare the second data according to the selection of the first and third electrodes 111_1 and 111_3 with the reference data and calculate a second correlation value between the first and third electrodes 111_1 and 111_3. In a similar manner, the correlator 122 may compare the data repeatedly recovered in operation S110 with the reference data, and calculate the correlation values repeatedly.

The correlator 122 may calculate the correlation values and then calculate the correlation sum of each of the first to the n-th electrodes 111_1 to 111_8. The correlator 122 may calculate the correlation sum of the target electrodes by summing the correlation values generated using the target electrode.

For example, in relation to the correlator 122, a first correlation value between the first and second electrodes 111_1 and 111_2, a second correlation value between the first and third electrodes 111_1 and 111_3, a third correlation value between the first and fourth electrodes 111_1 and 111_4, a fourth correlation value between the first and fifth electrodes 111_1 and 111_5, a fifth correlation value between the first and sixth electrodes 111_1 and 111_6, a sixth correlation value between the first and seventh electrodes 111_1 and 111_7, and a seventh correlation value between the first and eighth electrodes 111_1 and 111_8 may be correlation values generated using the first electrode 111_1. It is possible to calculate the first correlation sum of the first electrode 111_1 by summing the first to seventh correlation values generated using the first electrode 111_1.

In a similar manner, the correlator 122 may also calculate the second to eighth correlation sums of the second and eighth electrodes 111_2 to 111_8, respectively. Operation S120 will be described in more detail in FIG. 6.

In operation S130, the selector 123 may select the pair of electrodes according to the magnitude order of the correlation sums of the first to eighth electrodes 111_1 to 111_8. For example, the magnitude order of the correlation sums of the first to eighth electrodes 111_1 to 111_8 may be determined by sorting the first to eighth correlation sums of the first to eighth electrodes 111_1 to 111_8 calculated in operation S120 in descending order. The selector 123 may select the pair of optimal electrodes among the first to eighth electrodes 111_1 to 111_8 according to the magnitude order. Operation S130 will be described in more detail in FIG. 7

Figure 5:
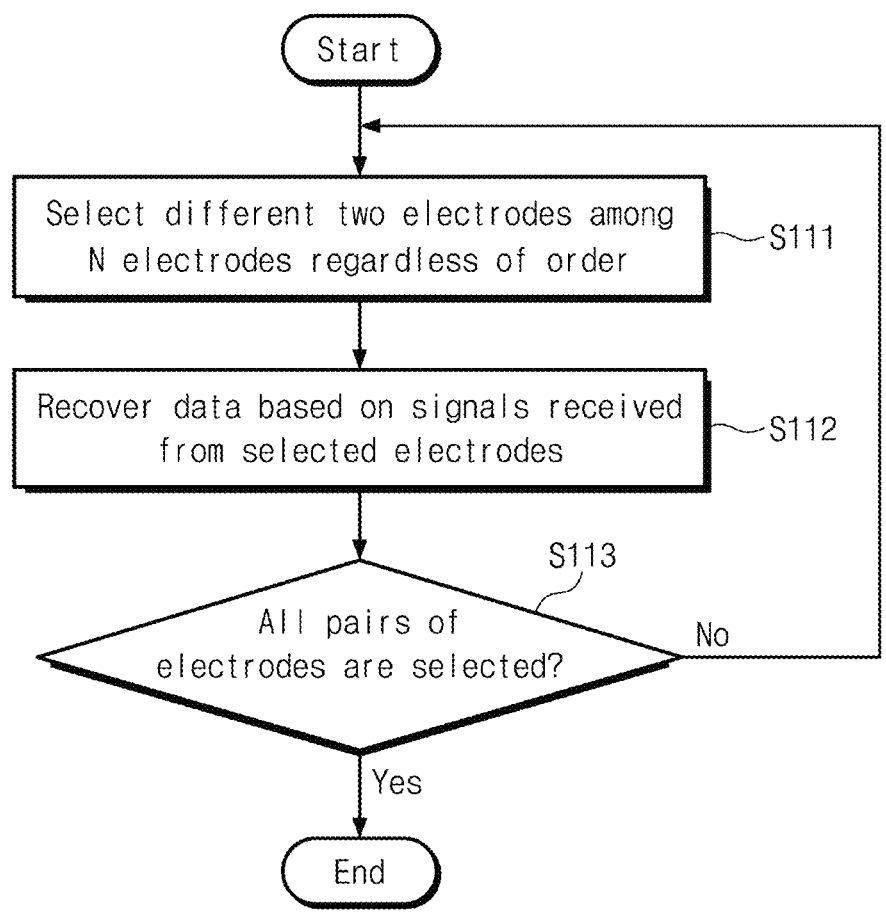
FIG. 5 is a flowchart illustrating an example of detailed operations of operation S110 of FIG. 4.

FIG. 5 is a flowchart illustrating an example of detailed operations of operation S110 of FIG. 4. This will be described with reference to FIGS. 2 to 4. In the same manner, in FIG. 5, it is assumed that the number of the first to n-th electrodes 111_1 to 111_n in FIG. 2 is eight.

In operation S111, the first and second multiplexers 112_1 and 112_2 may select two electrodes of the first to eighth electrodes 111_1 to 111_8 according to the control of the selector 123. In operation S112, the analog front end 110 may recover the clock and data based on the signals transmitted from the capsule endoscope 11 to the selected electrodes. In operation S113, the selector 123 may determine whether all pairs of electrodes are selected.

If all pairs of electrodes are selected, operation S110 may be terminated. If not, operations S111 and S112 may be repeated. For example, since n is assumed to be 8 in FIG. 5, the first and second multiplexers 112_1 and 112_2 may select the different electrodes among the first and eighth electrodes 111_1 to 111_8 according to the control of the selector 123 in total 28 times (8C2). If the selection is made 28 times by the first and second multiplexers 112_1 and 112_2 of the first to eighth electrodes 111_1 to 111_8, operation S110 may be terminated. If not, operations S111 and S112 may be repeated.

Figure 6:
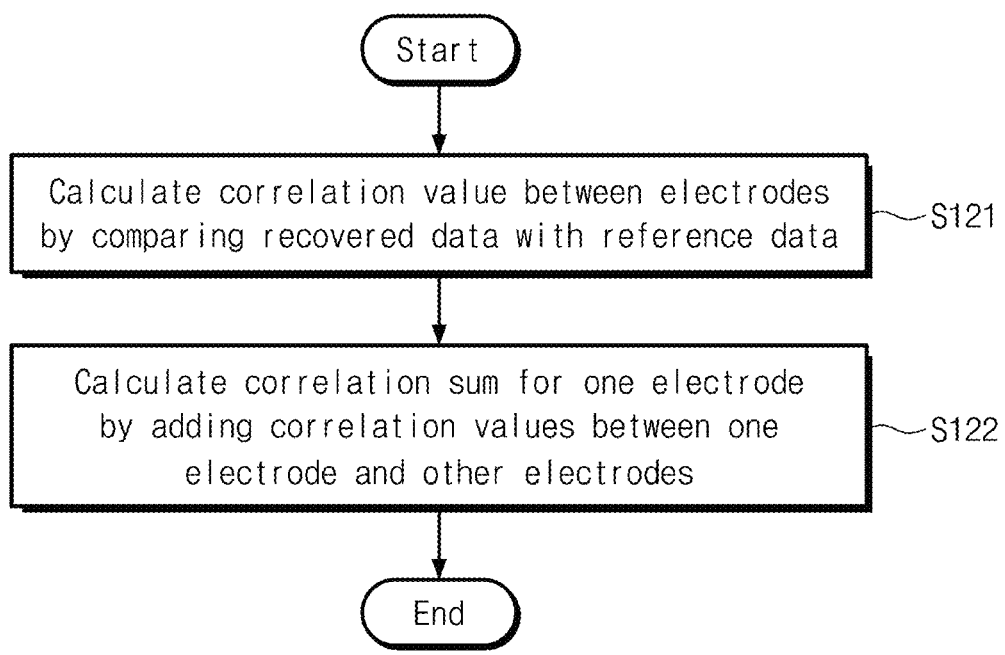
FIG. 6 is a flowchart illustrating an example of detailed operations of operation S120 of FIG. 4.

FIG. 6 is a flowchart illustrating an example of detailed operations of operation S120 of FIG. 4. FIG. 6 will be described with reference to FIGS. 2 to 4.

In operation S121, the digital receiver 120 may calculate the correlation value between the electrodes by comparing the data recovered by the analog front end 110 with the reference data. More specifically, the digital receiver 120 may calculate the first correlation value between the first and second electrodes by comparing the first data with the reference data. The digital receiver 120 may calculate the second correlation value between the first and third electrodes by comparing the second data with the reference data. The digital receiver 120 may calculate the third correlation value between the second and third electrodes by comparing the third data with the reference data. Of course, the digital receiver 120 may further calculate other correlation values between the other electrodes.

In operation S122, the digital receiver 120 may calculate the correlation sum for one electrode by adding correlation values between one electrode and the other electrodes. For example, when the number of the first and n-th electrodes 111_1 to 111_n is 3, the digital receiver 120 calculates the first correlation sum of the first electrode by adding a first correlation value between the first and second electrodes and a second correlation value between the first and third electrodes. The digital receiver 120 may calculate a second correlation sum of the second electrode by adding a first correlation value between the first and second electrodes and a third correlation value between the second and third electrodes. The digital receiver 120 may calculate a third correlation sum of the third electrode by adding a second correlation value between the first and third electrodes and a third correlation value between the second and third electrodes. Of course, as the number of the first and nth electrodes 111_1 to 111_n increases, the digital receiver 120 may further calculate other correlation sums of the other electrodes.

Figure 7:
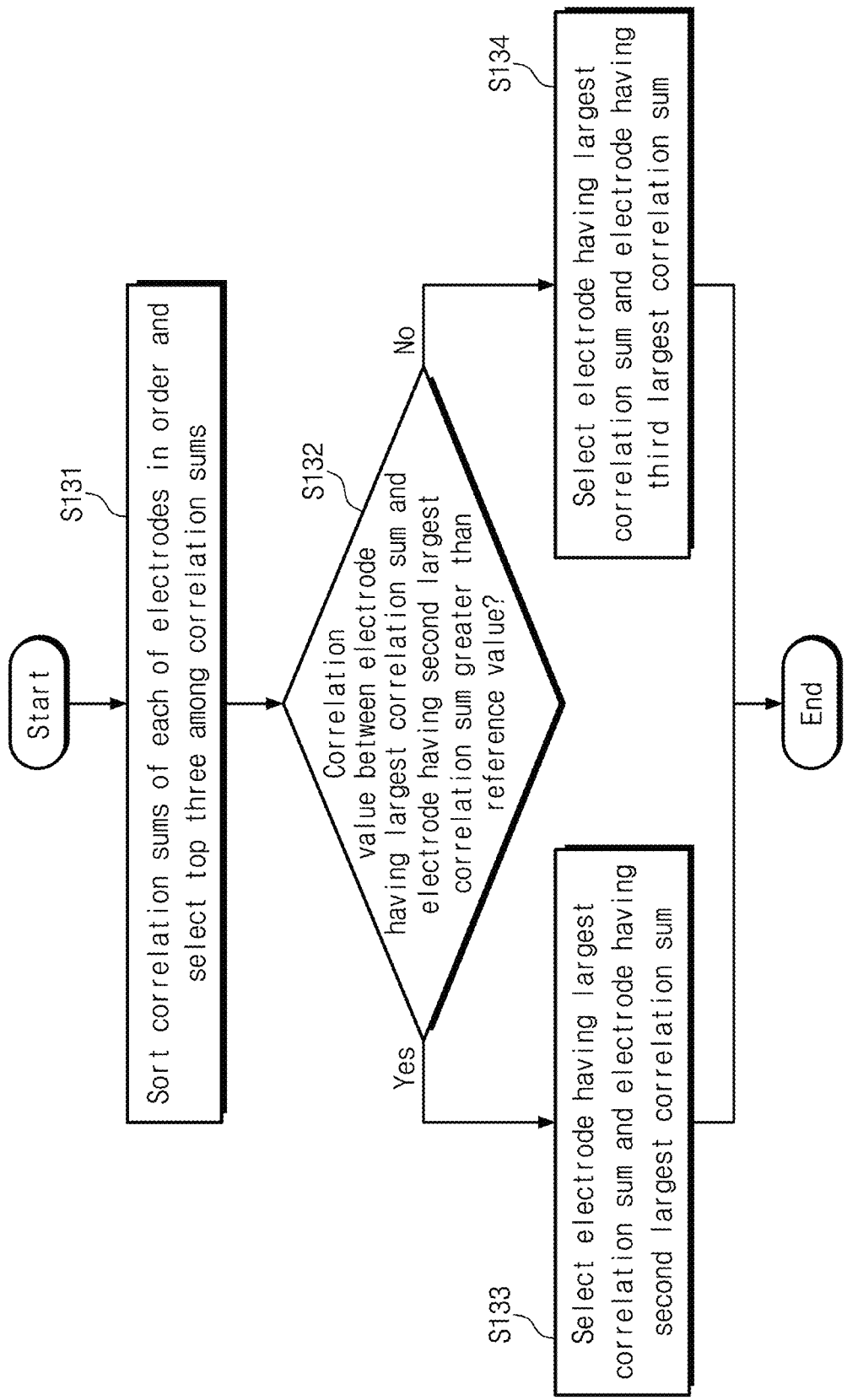
FIG. 7 is a flowchart illustrating an example of detailed operations of operation S130 of FIG. 4.

FIG. 7 is a flowchart illustrating an example of detailed operations of operation S130 of FIG. 4. FIG. 7 will be described with reference to FIGS. 2 to 4.

In operation S131, the selector 123 of the digital receiver 120 may sort the first to n-th correlation sums of the first to n-th electrodes 111_1 to 111_n calculated in operation S120. For example, the selector 123 may sort the first to n-th correlation sums of the first to the n-th electrodes 111_1 to 111_n in descending or ascending order. In operation S131, the selector 123 may select the top three correlation sums among the first to n-th correlation sums. The selector 123 may select the electrode having the largest correlation sum and the electrode having the second largest correlation sum as a pair of optimal electrodes or select the electrode having the largest correlation sum and the electrode having the third largest correlation sum as a pair of optimal electrodes In step S132, the selector 123 may find the electrode having the largest correlation sum and the electrode having the second largest correlation sum among the first to n-th electrodes 111_1 to 111_n. The selector 123 may determine whether the correlation value between the electrode having the largest correlation sum and the electrode having the second largest correlation sum is equal to or greater than the reference value. If the correlation value is greater than or equal to the reference value, operation S133 may be performed. If not, operation S134 may be performed.

In operation S132, the reference value may be used to determine whether the two electrodes may receive signals stably and accurately from the capsule endoscope 11, may be predetermined, and may be changed according to the channel environment. Operation S132 will be described in more detail with the example figures in FIG. 8.

In operation S133, the selector 123 may control the first and second multiplexers 112_1 and 112_2 to select the electrode having the largest correlation sum and the electrode having the second largest correlation sum. If the correlation value between the electrode having the largest correlation sum and the electrode having the second largest correlation sum is equal to or greater than the reference value, the two electrodes may receive data stably and accurately from the capsule endoscope 11. The digital receiver 120 may receive image data from the capsule endoscope 11 through the electrode having the largest correlation sum and the electrode having the second largest correlation sum. Operation S133 will be described in more detail with the example figures in FIG. 8.

In operation S134, the selector 123 may control the first and second multiplexers 112_1 and 112_2 to select the electrode having the largest correlation sum and select the electrode having the third largest correlation sum instead of the electrode having the second largest correlation sum. If the correlation value between the electrode having the largest correlation sum and the electrode having the second largest correlation sum is less than the reference value, there may be a reception error between the two electrodes and the capsule endoscope 11 of FIG. 1. The digital receiver 120 may receive image data from the capsule endoscope 11 through the electrode having the largest correlation sum and the electrode having the third largest correlation sum. Operation S134 will be described in more detail with the example figures in FIG. 8 in the same manner.

In an embodiment, the selector 123 does not select an electrode having the largest correlation sum and an electrode having the second largest correlation sum directly as a pair of optimal electrodes. Before selecting the electrode having the largest correlation sum and the electrode having the second largest correlation sum as a pair of optimal electrodes, the selector 123 may first determine whether the correlation value between the electrodes is equal to or greater than the reference value. Since the correlation sum of the electrodes is a value obtained by adding all the correlation values between the electrodes and the other electrodes, the correlation value between the electrodes having relatively large correlation sums may be less than the reference value. The selector 123 may not select the electrodes whose correlation value is less than the reference value through operations S132 and S134.

Figure 9:
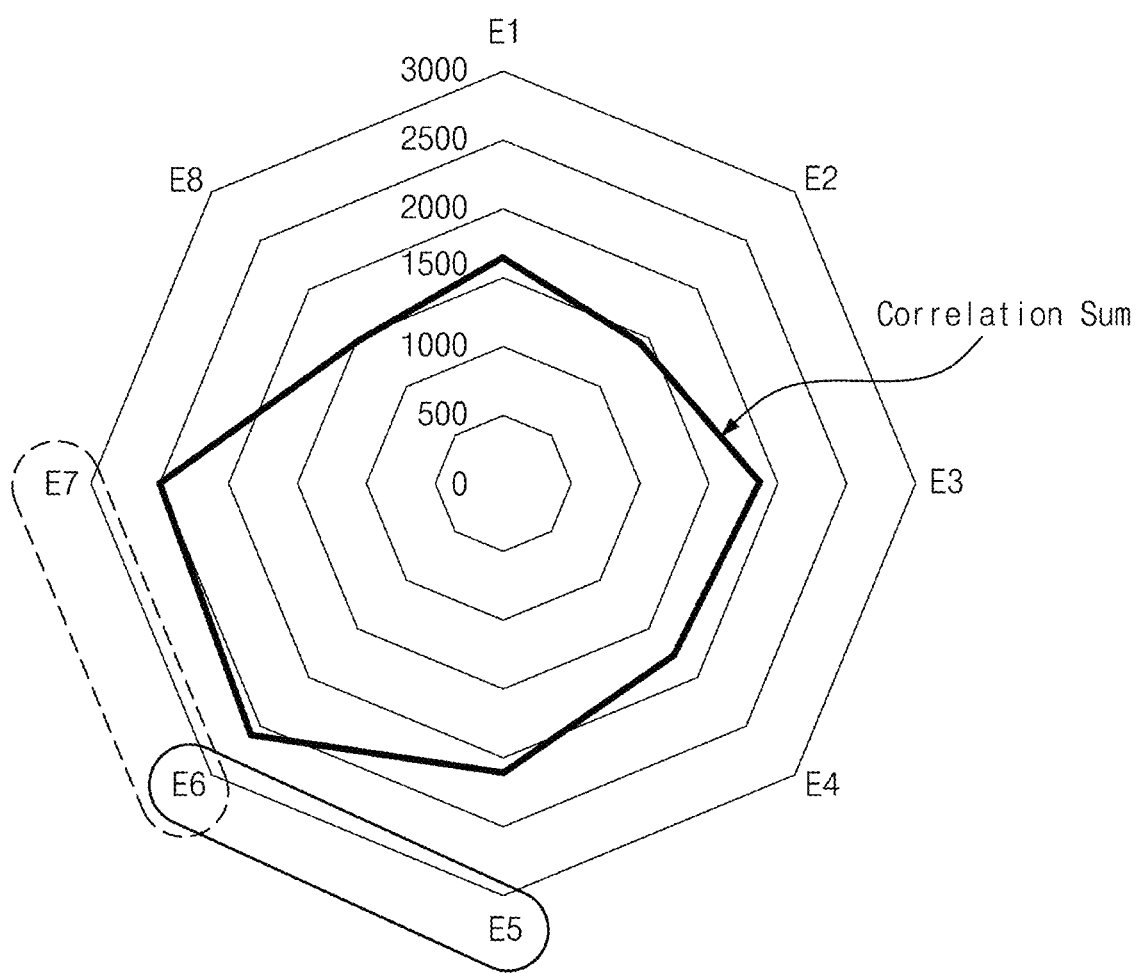
FIG. 9 is a graph showing the correlation sums of the electrodes of FIG. 8.

FIG. 8 is a table exemplarily showing correlation values between electrodes and correlation sums of electrodes according to the operations of FIG. 6. FIG. 9 is a graph showing the correlation sums of the electrodes of FIG. 8. FIGS. 8 and 9 will be described together and will be described with reference to FIGS. 2 to 7. In FIGS. 8 and 8, it is assumed that the number of the first to n-th electrodes 111_1 to 111_n in FIG. 2 is eight.

E1 to E8 may represent the first to eighth electrodes 111_1 to 111_8. The table of FIG. 8 shows correlation values between the electrodes calculated in operation S121 of FIG. 6. FIG. 8 and FIG. 9 exemplarily shows correlation sums of the first to eighth electrodes 111_1 to 111_8 calculated in operation S122 of FIG. 6.

For example, as shown in FIG. 8, the correlation sum of the sixth electrode E6 (111_6) is 2636, which may be larger than other correlation sums. The correlation sum of the seventh electrode E7 (111_7) is 2492, which may be larger than other correlation sums except for the correlation sum of the sixth electrode E6 (111_6). Therefore, the electrode having the largest correlation sum may be the sixth electrode E6 (111_6) and the electrode having the second largest correlation sum may be the seventh electrode E7 (111_7).

The selector 123 may determine whether the correlation value between the sixth electrode E6 (111_6) and the seventh electrode E7 (111_7) is equal to or greater than the reference value in operation S132. For example, the reference value is assumed to be 350. In FIG. 8, the correlation value between the sixth electrode E6 (111_6) and the seventh electrode (E7, 111_7) is 337, which may be smaller than the reference value. Accordingly, the selector 123 may perform operation S134. In FIG. 8, the correlation sum of the fifth electrode E5 (111_5) is 2130, which may be larger than other correlation sums except for the correlation sums of the sixth electrode E6 (111_6) and the seventh electrode E7 (111_7). As a result, the selector 123 may control the first and second multiplexers 112_1 and 112_2 to select the sixth electrode E6 (111_6) having the largest correlation sum and the fifth electrode E5 (111_5) having the third largest correlation sum.

Referring to FIG. 9, the sixth electrode E6 (111_6) may be the electrode having the largest correlation sum, and the seventh electrode E7 (111_7) may be the electrode having the second largest correlation sum. As described above, the selector 123 does not directly select the sixth electrode E6 (111_6) and the seventh electrode E7 (111_7) as a pair of optimal electrodes. The selector 123 may select the fifth electrode E5 (111_5) and the sixth electrode E6 (111_6) as a pair of optimal electrodes based on the comparison result of the correlation value between the sixth electrode E6 (111_6) and the seventh electrode E7 (111_7) and the reference value.

Figure 10:
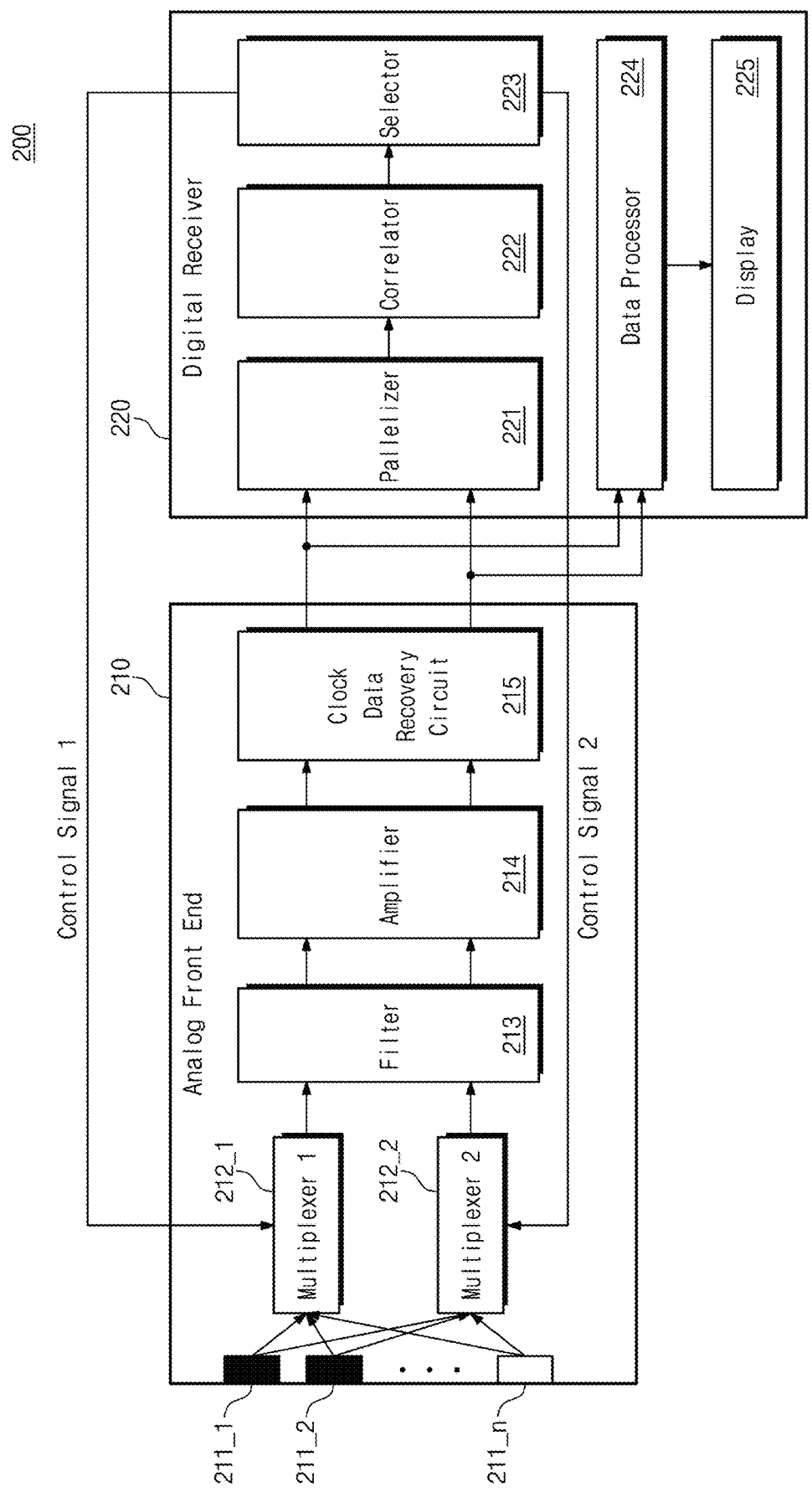
FIG. 10 is a block diagram exemplarily illustrating an electrode selection device according to another embodiment of the inventive concept.

FIG. 10 is a block diagram exemplarily illustrating an electrode selection device according to another embodiment of the inventive concept. Referring to FIG. 10, an electrode selection device 200 may include an analog front end 210 and a digital receiver 220. Here, the analog front end 210 may be substantially the same as the analog front end 110 of FIG. 2. Referring to FIG. 2, a digital receiver 220 may include a parallelizer 221, a correlator 222, a selector 223, a data processor 224, and a display 225. Here, the parallelizer 221, correlator 222, and selector 223 may be substantially identical to the parallelizer 121, correlator 122, and selector 123 of FIG. 2, respectively.

The data processor 224 may process the clock and data provided from the analog front end 210. Here, the image data provided from the analog front end 210 may correspond to data transmitted through a pair of optimal electrodes from the capsule endoscope 11 of FIG. 1, which is determined by operation S110 including operations S111 to S113, operation S120 including operations S121 and S122, and operation S130 including operations S131 to S134.

The display 225 may visually express the image data transmitted from the capsule endoscope 11 of FIG. 1. The display 225 may output image data. In an embodiment, the display 225 may include a liquid crystal display (LCD) and a light emitting diode (LED).

In an embodiment, the components 212_1, 212_2, 213, 214, 215, 221, 222, 223, and 224 of the electrode selection device 200 may be implemented using various semiconductor devices such as system-on-chip (SoC), application specific integrated circuit (ASIC), a field programmable gate array (FPGA), and the like.

The electrode selection device according to an embodiment of the inventive concept may select a pair of optimal electrodes based on the correlation sums of the electrodes. Thus, the electrode selection device may stably and accurately receive data from the capsule endoscope through the optimal electrodes.

Although the exemplary embodiments of the inventive concept have been described, it is understood that the inventive concept should not be limited to these exemplary embodiments but various changes and modifications may be made by one ordinary skilled in the art within the spirit and scope of the inventive concept as hereinafter claimed.

What is claimed is:

1. An electrode selection device communicating with a capsule endoscope, the device comprising:
   an analog front end configured to recover first data based on first signals transmitted from the capsule endoscope to a first electrode and a second electrode, recover second data based on second signals transmitted from the capsule endoscope to the first electrode and a third electrode, and recover third data based on third signals transmitted from the capsule endoscope to the second electrode and the third electrode; and
   a digital receiver configured to calculate, based on the first to third data, a first correlation value between the first and second electrodes, a second correlation value between the first and third electrodes, and a third correlation value between the second and third electrodes,
   wherein the digital receiver is further configured to:
   calculate a first correlation sum obtained by adding first and second correlation values generated using the first electrode, a second correlation sum obtained by adding the first and third correlation values generated using the second electrode, and a third correlation sum obtained by adding the second and third correlation values generated using the third electrode,
   compare magnitudes of the first to third correlation sums,
   when the first correlation sum is greater than the second correlation sum and the second correlation sum is greater than the third correlation sum, compare the first correlation value with a reference value,
   if the first correlation value is equal to or greater than the reference value, select the first and second electrodes as a receiving electrode pair; and
   if the first correlation value is less than the reference value, select the first and third electrodes as the receiving electrode pair.

2. The electrode selection device of claim 1, wherein each of the capsule endoscope and the digital receiver stores reference data;
   the capsule endoscope transmits the first to third signals to the analog front end based on the reference data; and
   the digital receiver compares the first data with the reference data to calculate the first correlation value, compares the second data with the reference data to calculate the second correlation value, and compares the third data with the reference data to calculate the third correlation value.

3. The electrode selection device of claim 1, wherein the digital receiver calculates the first correlation sum by adding the first and second correlation values, calculates the second correlation sum by adding the first and third correlation values, and calculates the third correlation sum by adding the second and third correlation values.

4. The electrode selection device of claim 1, wherein the analog front end comprises:
   multiplexers configured to select the first and second electrodes among the first to third electrodes, respectively, and output the first signals;
   a filter configured to filter the first signals;
   an amplifier configured to amplify the filtered first signals; and
   a clock data recovery circuit configured to recover a clock and the first data based on the amplified first signals and provide the clock and the first data to the digital receiver.

5. The electrode selection device of claim 4, wherein the digital receiver comprises:
   a parallelizer configured to parallelize the first data;
   a correlator configured to calculate the first correlation value based on the first data; and
   a selector configured to control the multiplexers such that the multiplexers select the first and second electrodes, respectively.

6. The electrode selection device of claim 1, wherein the digital receiver further comprises:
   a data processor configured to process fourth data provided by the analog front end after the receiving electrode pair is selected; and
   a display configured to output the fourth data.

7. An operation method of an electrode selection device communicating with a capsule endoscope, the method comprising:
   recovering first data based on first signals transmitted from the capsule endoscope to a first electrode and a second electrode and calculating a first correlation value between the first electrode and the second electrode based on the first data;
   recovering second data based on second signals transmitted from the capsule endoscope to the first electrode and a third electrode and calculating a second correlation value between the first electrode and the third electrode based on the second data;
   recovering third data based on third signals transmitted from the capsule endoscope to the second electrode and the third electrode and calculating a third correlation value between the first electrode and the third electrode based on the third data;
   calculating a first correlation sum of the first electrode, a second correlation sum of the second electrode, and a third correlation sum of the third electrode by separately adding the first to third correlation values; and
   selecting a receiving electrode pair among the first to third electrodes based on the first to third correlation sums,
   wherein the selecting of the receiving electrode pair comprises:
   comparing magnitudes of the first to third correlation sums,
   when the first correlation sum is greater than the second correlation sum and the second correlation sum is greater than the third correlation sum, comparing the first correlation value with a reference value,
   if the first correlation value is equal to or greater than the reference value, selecting the first and second electrodes as the receiving electrode pair; and if the first correlation value is less than the reference value, selecting the first and third electrodes as the receiving electrode pair.

8. The operation method of claim 7, wherein the calculating of the first to third correlation values comprises:
comparing the first data with reference data to calculate the first correlation value;
comparing the second data with the reference data to calculate the second correlation value; and
comparing the third data with the reference data to calculate the third correlation value.

9. The operation method of claim 7, wherein the calculating the first to third correlation sums comprises:
calculating the first correlation sum of the first electrode by adding the first and second correlation values;
calculating the second correlation sum of the second electrode by adding the first and third correlation values; and
calculating the third correlation sum of the third electrode by adding the second and third correlation values.

* * * * *